United States Patent [19]

Grim

[11] Patent Number: 4,977,891
[45] Date of Patent: Dec. 18, 1990

[54] VARIABLE SUPPORT ANKLE BRACE

[75] Inventor: Tracy E. Grim, Broken Arrow, Okla.

[73] Assignee: Royce Medical Company, Westlake Village, Calif.

[21] Appl. No.: 433,565

[22] Filed: Nov. 8, 1989

[51] Int. Cl.⁵ ................................................ A61F 5/00
[52] U.S. Cl. ................................ 128/80 H; 128/87 R
[58] Field of Search ............... 128/80 A, 80 H, 80 R, 128/83, 87 R

[56] References Cited

U.S. PATENT DOCUMENTS

| | | | |
|---|---|---|---|
| 2,552,711 | 5/1951 | Dunker | 36/3 |
| 2,560,591 | 7/1951 | Oltrogge | 36/3 |
| 2,676,422 | 4/1954 | Crawford | 36/3 |
| 3,029,530 | 4/1962 | Eaton | 36/3 |
| 3,331,146 | 7/1967 | Karras | 36/3 |
| 4,280,489 | 7/1981 | Johnson, Jr. | 128/80 |
| 4,414,760 | 11/1983 | Faiella | 36/29 |
| 4,505,269 | 3/1985 | Davies et al. | 128/87 R |
| 4,628,945 | 12/1986 | Johnson, Jr. | 128/80 |
| 4,805,601 | 2/1989 | Eischen, Sr. | 128/80 H |
| 4,844,094 | 7/1989 | Grim | 128/80 H |
| 4,865,023 | 9/1989 | Craythorne et al. | 128/80 H |

FOREIGN PATENT DOCUMENTS 2231817  4/1973  Fed. Rep. of Germany.

Primary Examiner—Robert A. Hafer
Assistant Examiner—Kerry Owens
Attorney, Agent, or Firm—Poms, Smith, Lande & Rose

[57] ABSTRACT

An ankle brace having two relatively rigid side supports with inflatable bladders attached to them. The side supports are connected at their bottom by a flexible strap upon which is mounted an air pump. The air pump is activated by walking and running and inflates the air bladders mounted on the side supports. The side supports are held firmly in place about the lower leg and ankle by straps. A relief valve and/or pin holes in the bladders prevent excessive pressure in the bladders and provide reduced support when the user is not active.

18 Claims, 3 Drawing Sheets

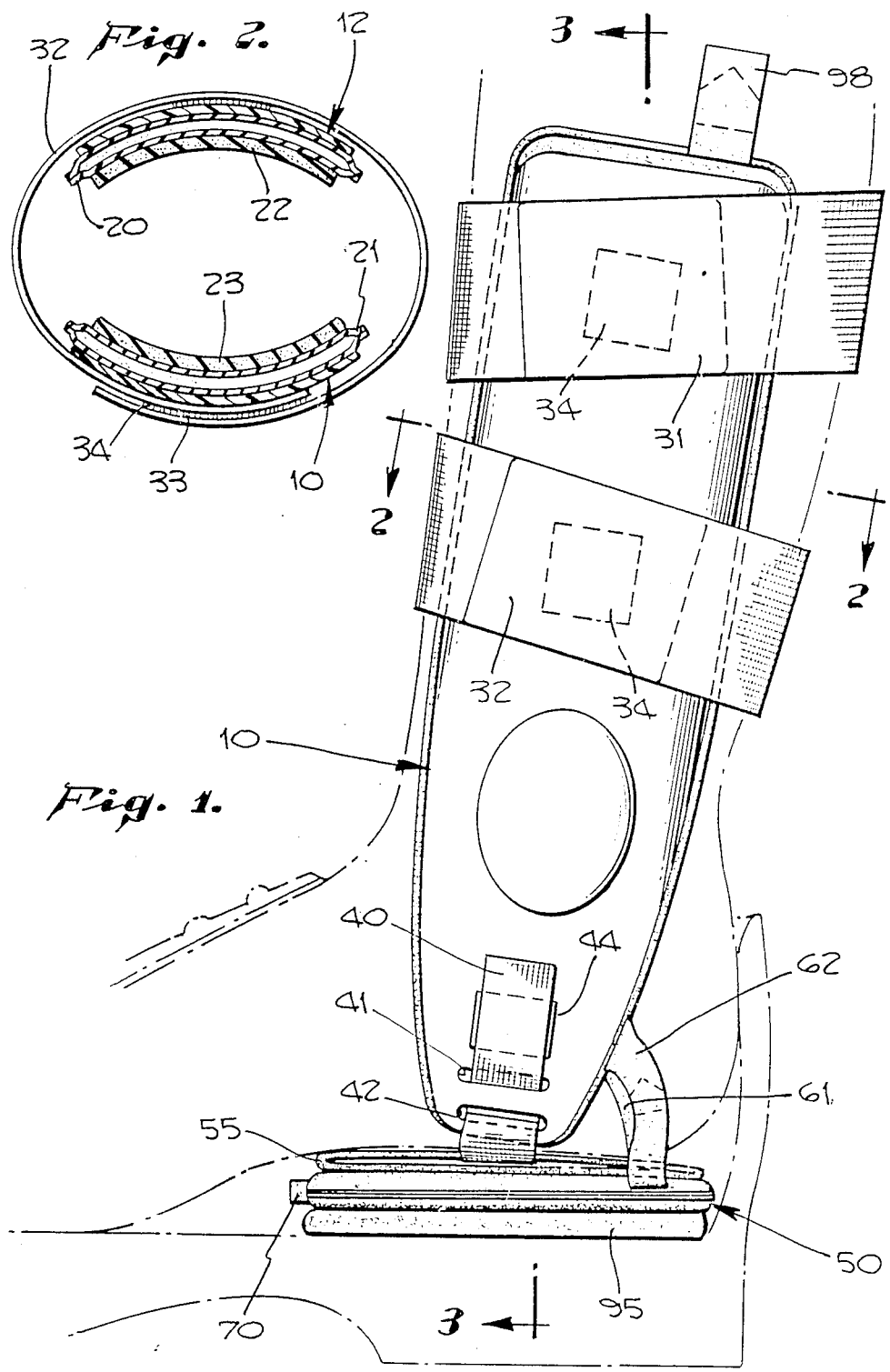

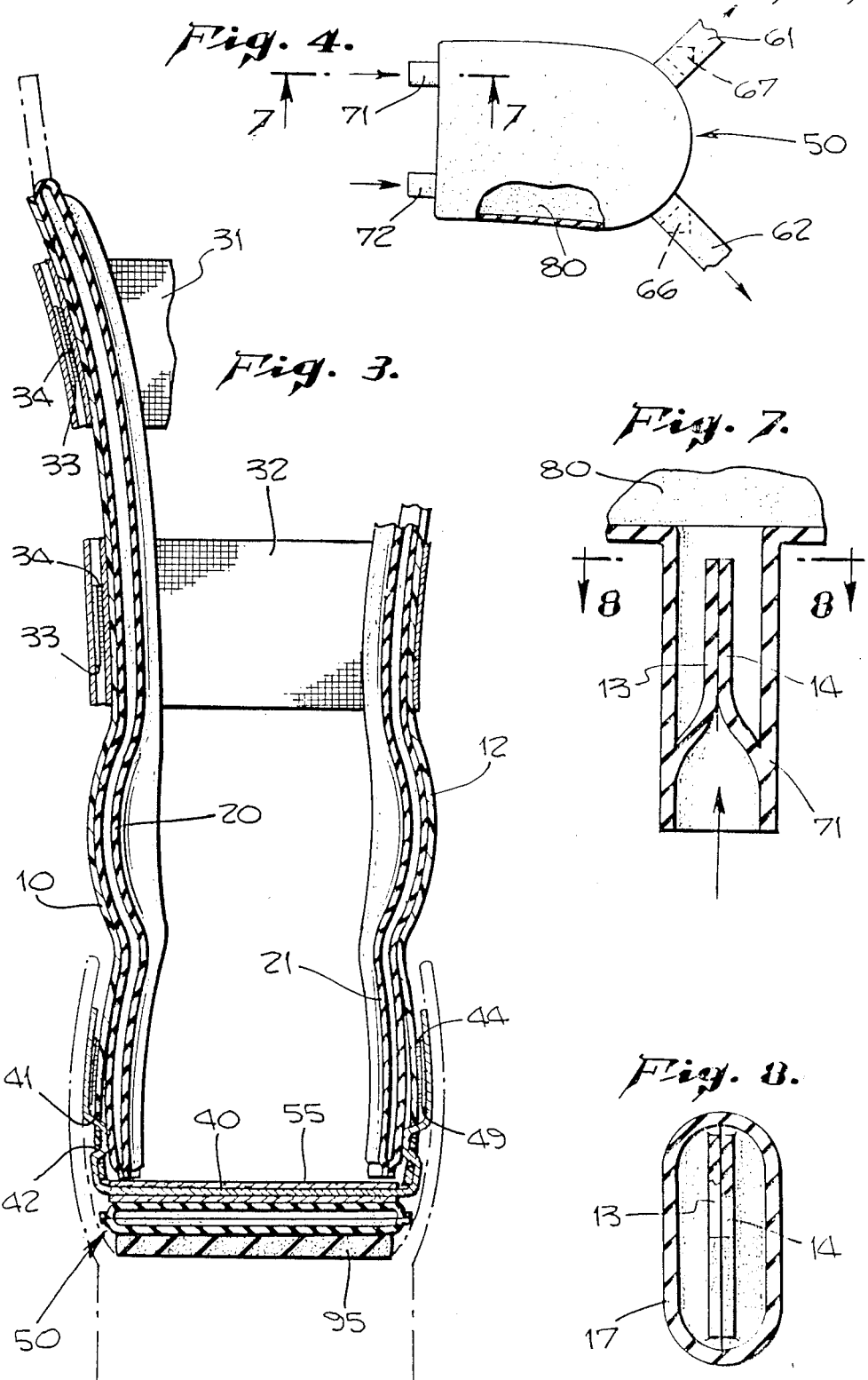

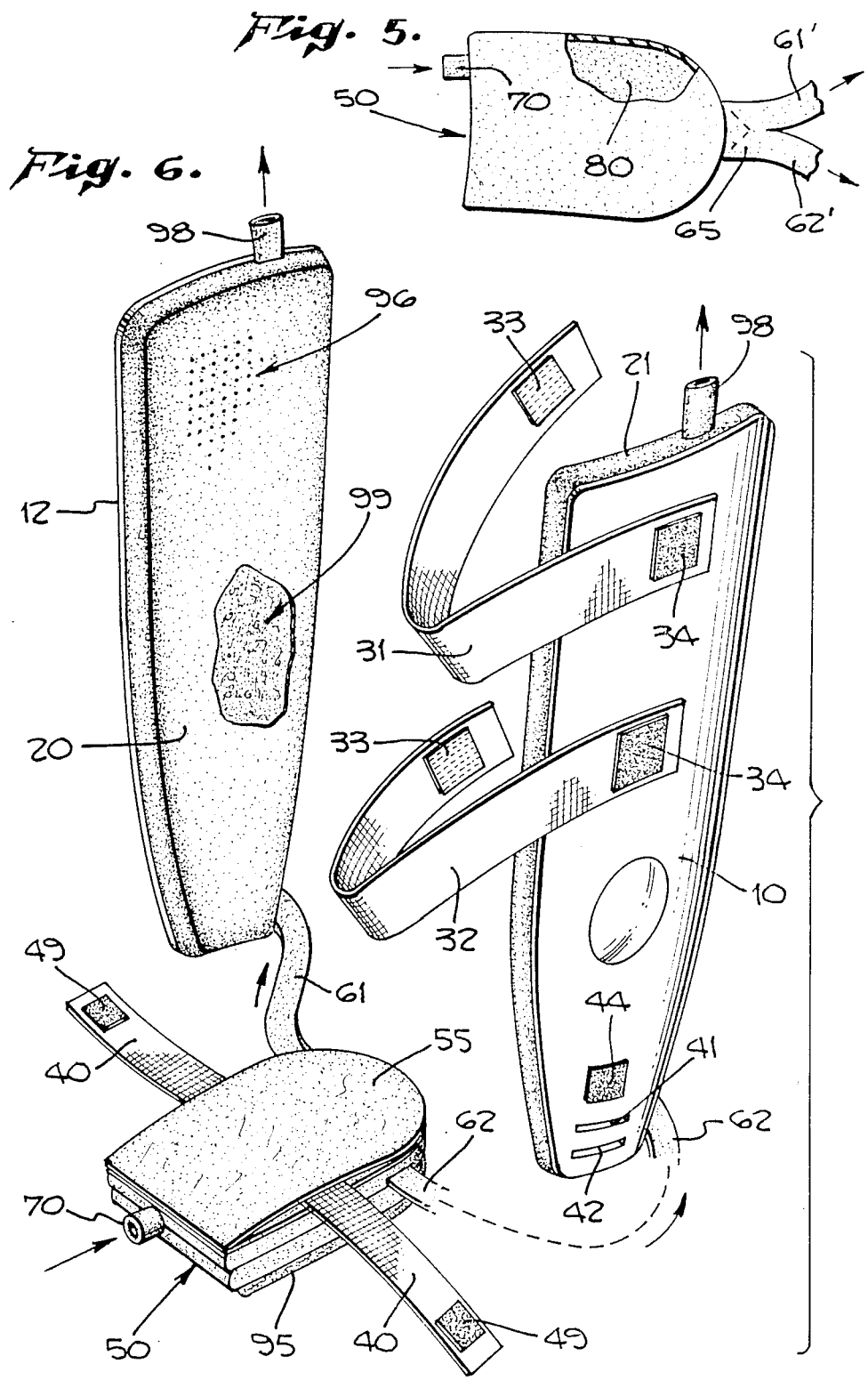

VARIABLE SUPPORT ANKLE BRACE

RELATED APPLICATION

Variable Support Shoe, Ser. No. 310,836, filed Feb. 14, 1989. Related copending application Ser. No. 310,836 filed Feb. 14, 1989, shows the use of an air pump and air bladder arrangements, integral with an athletic shoe, to provide increased support to the foot and ankle in an athletic shoe during activity, and decreased pressure and support during periods of inactivity.

FIELD OF THE INVENTION

The present invention relates to an orthopaedic device, and specifically to an ankle brace for stabilizing an ankle before and after injury. In particular, the ankle brace of the present invention stabilizes the ankle against inversion and eversion and anterior subluxation while allowing normal dorsiflexion and plantarflexion movement.

BACKGROUND OF THE INVENTION

It has previously been proposed to provide an ankle brace or orthopaedic apparatus, including air inflatable bladders as shown in Glenn W. Johnson, Jr.'s U.S. Pat. Nos. 4,280,489, granted July 28, 1981, and No. 4,628,945, granted Dec. 16, 1986 in which the apparatus is intended to be worn within a separate shoe and is inflatable with an external source of air pressure or is preinflated. In addition, various arrangements have been proposed for ventilating shoes by circulating air through the shoes. Typical patents showing this type of arrangement include M. Dunker, U.S. Pat. No. 2,552,711; D. W. Oltrogge, U.S. Pat. No. 2,560,591; A. C. Crawford, U.S. Pat. No. 2,676,422; C. N. Eaton, U.S. Pat. No. 3,029,530; E. Karras, U.S. Pat. No. 3,331,146; and James Faiella, U.S. Pat. No. 4,414,760. These patents disclose the use of an air pumping arrangement actuated by foot pressure for circulating air through a shoe, but do not include any orthopaedic support functions. Reference is also made to German publication designated OffenlegungSschrift No. 2321817, published Nov. 15, 1973. That publication shows a ski boot with a rigid sole and a pump mounted in the sole. The pump can be latched to an inactive state when the inflatable pads are pressurized.

After injury to an ankle, such as a fracture or severe ankle sprain, it may be necessary to completely immobilize the ankle through the use of a molded plaster or resin cast. However, once the injury has been stabilized, recovery may be hastened by removing the molded plaster or resin cast and using a removable functional walking brace so that the ankle can be exercised during healing. Also, if the injury is not severe enough to require complete immobilization, it may only be necessary to use a functional walking brace to stabilize the ankle against inversion (the foot rolling inward), eversion (the foot rolling outward) or anterior subluxation (partial dislocation) while still permitting the normal dorsiflexion and plantarflexion forward and rearward motion of the lower leg relative to the foot) movement of the ankle. However, less pressure and support is required when resting. Furthermore, it is undesirable to have the feet or ankles subject to substantial pressure while resting as this may inhibit circulation during rest periods.

It is therefore desirable to have an ankle brace which provides greater support and pressure to the ankle during walking and the like and less pressure upon the ankle and foot during periods of rest.

SUMMARY OF THE INVENTION

The present invention is a new and improved ankle brace which provides varying amounts of pressure and support to the foot and ankle. The brace has two side supports with inflatable bladders attached to the supports. The brace also includes a pump which is activated by walking or running and supplies air to the inflatable bladders. Also included are means for securing the side supports to firmly encase the ankle. The means for securing the side supports could be an arrangement of straps and D-rings, straps and velcro type fasteners or other appropriate systems.

The air bladders may have a high pressure release valving arrangement, and also be provided with bleed arrangements so that the bladders may not be inflated above a predetermined pressure and so that the air pressure in the bladders will gradually leak out over a period of time.

One-way valves may be provided, both at the inlet to the pump and at the outlet therefrom, leading to the air bladders. With the pump located under the user's foot, pressure will be drawn in whenever the foot is raised, and air will be pumped out to the air bladders whenever the foot engages the ground and the pump chamber is compressed. The bladders may have a bleed valve arrangement as mentioned above which may be either in the form of a specific physical valve, or this function may be provided through a series of small holes extending through the surface of the bladders.

The pump may be in the form of a relatively flat chamber underlying the heel of the user, and is normally resiliently biased so that the air chamber is expanded. Then, when the person's foot is applied downward onto the chamber, it is compressed and the air is forced into the support bladders. Subsequently, when the foot is raised, the pump chamber expands under the resilient force, and air is sucked into the pump chamber. This process is repeated until the support bladders reach their full rated pressure. At this pressure level, the release valve may prevent further build-up of pressure within the bladders, thus controlling the level of pressure against the ankle and foot and the resultant support.

The valves may be implemented by separate valves which may be purchased independently and installed in the interconnecting tubing, or they may be implemented by integral plastic parts in the form of flaps or resiliently mounted plugs which close and open to control the air flow in a manner similar to the separate or independent valves.

At the outlet from the pump, a single one-way valve may be provided or, alternatively, separate one-way valves may extend to each of the support bladders.

The advantage of the system of the present invention is that full support to the ankle and foot is provided when the user is active but, when the user is resting, the bladder arrangements permit a reduction of pressure in the bladders. Heavy support pressure is not applied during resting periods, and circulation is not impaired. Some level of support may be maintained by the use of a compressible filler dispensed within the bladders or outside the bladders. This system prevents undesired eversion, inversion and anterior subluxation caused by activity while allowing for reduced pressure during rest periods.

BRIEF DESCRIPTION OF THE DRAWINGS

FIG. 1 is a side view of the ankle brace as it would appear while being worn with the shoe cut away for clarity.

FIG. 2 is a cross-sectional view taken along plane indicated at II—II in FIG. 1.

FIG. 3 is a partially cut-away view of the ankle brace as it would appear while being worn.

FIG. 4 is an overhead view of the pump with two inlet valves.

FIG. 5 is an overhead view of the pump.

FIG. 6 is a partially exploded view of the present invention.

FIG. 7 shows a cross sectional view of a flap type valve taken along plan 7—7 in FIG. 4.

FIG. 8 is a cross sectional view of a flap type valve taken along the plane VIII—VIII shown in FIG. 7.

DETAILED DESCRIPTION

With reference to FIGS. 1 and 6, the ankle brace of the present invention includes a pair of side supports 10 and 12 preferably made of vacuum molded plastic, having sufficient thickness and other properties so that they are relatively stiff or rigid; and they are shaped so as to fit about the lower leg and ankle and are at least eight inches in length. Inflatable bladders 20 and 21 (shown in FIGS. 2 and 3) are mounted on the side supports 10 and 12 on the side of the side support which faces in toward the leg. The inflatable bladders 20 and 21 can be attached to the side supports 10 and 12 by double-sided adhesive or any other suitable means. The inflatable bladders can be formed from two sheets of plastic heat-sealed along their edges to form an inflatable bag.

The side supports may be securely attached around the leg and ankle using the two securing straps 31 and 32 as shown in the cross-sectional view of FIG. 2 and the cut-away view of FIG. 3. These straps also include velcro portions on their outside surfaces as shown by velcro material 33 and with velcro material 34 at the end portion of the straps. The velcro 34 is attached to the side support 10. As shown in FIGS. 1 and 2, the straps may be tightly drawn around the leg and secured using the velcro material so that the ankle brace securely and firmly supports the ankle.

Interconnecting the two side supports 10 and 12 toward their bottoms is the bottom strap 40. Attached to the bottom strap 40 is a pad member 55, made of a flexible cushioning type material such as polyurethane foam. The bottom strap 40 may include a surface 49 of velcro material with the bottom strap being adjustable through the use of double openings 41 and 42 in the side supports. The ends of the bottom strap 40 may be fixed in position with the use of additional velcro material 44 located on the outside of the side support members as shown in FIG. 3 on side support member 10.

FIG. 1 shows the pump 50 located under the pad member 55 and connected to the bottom strap 40. As shown in FIG. 1, the pump 50 would be located under the wearer's heel. Referring now to FIG. 5, the pump 50 has an inlet valve 70, and an outlet valve 65. The pump also includes a variable volume air chamber 80 having upper and lower flexible sidewalls, and a biasing material 95 which may be a resilient flexible porous pad, and which normally biases the chamber 80 to its expanded volume configuration. When a wearer steps down on the pump 50, the outlet valve 65 opens, and the inlet valve 70 is closed. When the foot is raised, the resilient pad expands the chamber 80, drawing air in through the inlet valve 70, while the outlet valve 65 is closed. Inlet valve 70 and outlet valve 65 may be ball and spring-type valves, but it is to be understood that any appropriate type of one-way valve could be employed.

Extending upward from the outlet valve 65 are two small diameter tubes 61' and 62', each of which is connected to one of the inflatable bladders 20. Alternatively, separate one-way valves 66 and 67, shown in FIG. 4, could be placed in each of the small diameter tubes instead of using one outlet valve 65. It should be noted that the resilient pad 95 used to bias the variable volume air chamber 80 could be replaced with a metal spring, or other suitable resilient material which would bias the chamber to its expanded volume configuration when the user raises his foot and releases pressure from the pump.

FIGS. 4 and 5 show two alternative placements of the inlet valves of the pump 50. FIG. 4 shows the inlet valve 70 replaced with dual inlet valves 71 and 72 placed to either side of the front of the pump. FIG. 5 shows the inlet valve 70 placed toward the wearer's instep in the front of the pump. Also shown in FIG. 4 are the two small diameter tubes 61 and 62 as they could be arranged if each contained an outlet valve 66 and 67 similar to outlet valve 65.

The two inlet valves 71 and 72 of FIG. 4 could alternatively be of a fairly flat flap-type valve. Such a valve is pictured in FIGS. 7 and 8. In such a valve, air drawn in as indicated by the arrow forces the two sealing flaps 13 and 14, which are normally biased together, apart which allows the air to flow through the valve. Air forced in the direction opposite to that indicated by the arrow, toward the flaps, forces flaps 13 and 14 together and they create a substantially airtight seal. This flap-type valve could be made of flexible plastic or rubber and may be more comfortable than a rigid valve when used under the wearer's foot. FIGS. 1 and 6 show the release valve 98, which is an over pressure release and a bleed valve for the inflatable bladder 20. More specifically, a slight amount of air is permitted to bleed from the valve 98 continuously over prolonged periods of time. Further, the relief valve 98 changes state to release air from the inflatable bladder when pressure supplied by the pump becomes excessive, so the maximum pressure level is not exceeded within the inflatable bladders when the wearer of the ankle brace is active.

As an alternative to the bleed function which may be included in relief valve 98, the bladders 20 may be provided with a number of very small holes 96 shown in FIG. 6. The holes 96, which may be in the nature of pinholes, may provide the bleed function which may otherwise be accomplished through the relief valve 98. Also, the position of the relief valve 98 is not necessarily limited to the position shown.

An alternative embodiment of the present invention further includes a closed cell foam pad disposed within the inflatable bladder 20. This is shown in FIG. 6 as 99. The pad can be used to provide a minimum level of support and padding. Alternatively, the pad may be attached to the outside of inflatable bladders 20 and 21 on the side towards the wearer's leg as indicated by 22 and 23 in FIG. 2. The pad may also be open cell foam and may be placed between the bladders and the side supports (not shown).

In conclusion, it is to be understood that the foregoing detailed description relates to a presently preferred embodiment of the present invention. Various changes and modifications may be made without departing from the spirit and scope of the present invention. Thus, by way of example and not of limitation, the various valve structures which have been shown as separate elements may be implemented by constructions formed from the materials out of which the pump and/or bladders are made. Thus, plastic flaps may form one-way valve constructions as shown in FIGS. 7 and 8 and the pressure release valve may be formed of a plastic, rubber or other material which is resiliently biased closed, and forced open when a predetermined level of pressure is reached. Also, the release valve 98 may be preset to a maximum pressure at which it will release air from the inflatable bladder or it may be adjustable. It is further noted that a pump or bellows may be located under the arch or forefoot, instead of or in addition to that located under the heel, as shown in the drawings. Accordingly, the present invention is not limited to the constructions precisely as shown in the drawings or described in the detailed description.

I claim:

1. An ankle brace for insertion into a shoe comprising:
   a pair of side supports for fitting about the lower leg on both sides and with the side supports having a configuration to support both sides of the ankle;
   inflatable bladders mounted on said side supports to provide a cushion between the ankle and the side supports, and for applying supporting pressure;
   means for securing the side supports to firmly encase the ankle;
   flexible means for extending between the side supports toward the bottom of said supports;
   means including a pump secured to said flexible means and actuated by walking or running activity for supplying air to said inflatable bladders; and
   a one way valve interconnecting said pump and said bladders;
   whereby walking or running activity increases the air pressure in said inflatable bladders and provides additional support to the foot and ankle against inversion, eversion or anterior subluxation while permitting plantarflexion and dorsiflexion.

2. An ankle brace as defined in claim 1 wherein said side supports are formed of relatively stiff or rigid material and are limited in extent to the sides of the leg, ankle, and heel of the user.

3. An ankle brace as defined in claim 1 wherein said ankle brace includes at least one one-way inlet valve for supplying air to said pump means.

4. An ankle brace as defined in claim 1 wherein said pump includes a variable volume air chamber and resilient means for biasing said chamber to its expanded configuration.

5. An ankle brace as defined in claim 1 wherein said ankle brace includes relief means for releasing air from said inflatable bladders over a predetermined period of time which is relatively long compared to the periodicity of normal walking steps.

6. An ankle brace for insertion into a shoe comprising:
   a pair of side supports for fitting about the lower leg on both sides and with the side supports having a configuration to support both sides of the ankle;
   inflatable bladders mounted on said side supports to provide a cushion between the ankle and the side supports, and for applying supporting pressure;
   means for securing the side supports to firmly encase the ankle;
   flexible means for extending between the side supports toward the bottom of said supports;
   means including a pump secured to said flexible means and actuated by walking or running activity for supplying air to said inflatable bladders; and
   a plurality of tiny holes in said bladders for releasing air from said bladders over a predetermined period of time which is relatively long compared to the periodicity of normal walking steps.

7. An ankle brace as defined in claim 1 wherein said flexible means is adjustable to adjust the distance between the side supports at the bottom of said side supports.

8. An ankle brace as defined in claim 1 wherein said inflatable bladders contain compressible filler material.

9. An ankle brace as defined in claim 8 wherein said compressible filler means comprises a closed cell foam pad disposed within said inflatable bladder.

10. An ankle brace as defined in claim 1 wherein said pump is relatively flat and is attached to said flexible means, whereby said pump is located generally under the wearer's heel when said ankle brace is worn.

11. An ankle brace as defined in claim 1 wherein said side supports have a relatively thin configuration such that a shoe can be worn over said ankle brace.

12. An ankle brace for insertion into a shoe comprising:
   a pair of side supports for fitting about the lower leg on both sides with a configuration to support both sides of the ankle, said side supports being formed of relatively stiff or rigid material, and being limited in extent to the sides of the leg, ankle, and heel of the user;
   inflatable bladders mounted on said side supports to provide a cushion between the ankle and the side supports, and for applying supporting pressure;
   means for securing the side supports to firmly encase the ankle;
   flexible means extending between the side supports toward the bottom of said supports;
   a pump actuated by walking or running activity for supplying air to said inflatable bladders, having a one way inlet valve;
   a one way valve interconnecting said pump and said bladders;
   a one way inlet valve for air supplied to said pump; and
   relief means for releasing air from said inflatable bladders over a predetermined period of time which is relatively long compared to the periodicity of normal walking;
   whereby walking or running activity increases the air pressure in said inflatable bladders and provides additional support to the foot and ankle against inversion, eversion or anterior subluxation while permitting plantarflexion and dorsiflexion, and the increased pressure is released within a few minutes after the activity stops to minimize pressure on the foot and ankle while resting.

13. An ankle brace as defined in claim 12 wherein said pump means includes a variable volume air chamber and resilient means for biasing said chamber to its expanded configuration.

14. An ankle brace as defined in claim 12 wherein said ankle brace includes relief means for releasing air from said inflatable bladders over a predetermined period of time which is relatively long compared to the periodicity of normal walking steps.

15. An ankle brace for insertion into a shoe comprising:
- a pair of side supports for fitting about the lower leg on both sides with a configuration to support both sides of the ankle, said side supports being formed of relatively stiff or rigid material, and being limited in extent to the sides of the leg, ankle, and heel of the user;
- inflatable bladders mounted on said side supports to provide a cushion between the ankle and the side supports, and for applying supporting pressure;
- means for securing the side supports to firmly encase the ankle;
- flexible means extending between the side supports toward the bottom of said supports;
- a pump actuated by walking or running activity for supplying air to said inflatable bladders; and
- a plurality of tiny holes in said bladders for releasing air from said bladders over a predetermined period of time which is relatively long compared to the periodicity of normal walking;
- whereby walking or running activity increases the air pressure in said inflatable bladders and provides additional support to the foot and ankle against inversion, eversion or anterior subluxation while permitting plantarflexion and dorsiflexion, and the increased pressure is released with a few minutes after the activity stops to minimize pressure on the foot and ankle while resting.

16. An ankle brace as defined in claim 15 wherein said relief means limits the maximum pressure in said inflatable bladders.

17. An ankle brace as defined in claim 12 wherein a pad member is disposed between said inflatable bladders and the lower leg and ankle.

18. An ankle brace for insertion into a shoe comprising:
- a pair of substantially rigid side supports at least eight inches long for fitting about the lower leg on both sides having a configuration to support both sides of the ankle and leave space between the front and rear edges of the supports so that the plantarflexion and dorsiflexion motions of the ankle are not impeded;
- inflatable bladders mounted on said side supports to provide a cushion between the ankle and the side supports, and for applying supporting pressure;
- means for securing the side supports to one another and to firmly support the ankle;
- flexible means extending between the side supports toward the bottom of said supports for underlying the heel of the user's foot;
- a pump mounted on said flexible means and actuated by walking or running activity for supplying air to said inflatable bladders; and
- relief means for automatically releasing air from said inflatable bladders over a predetermined period of time which is relatively long compared to the periodicity of normal walking and for limiting the maximum pressure in said inflatable bladders;
- whereby walking or running activity increases the air pressure in said inflatable bladders and provides additional support to the foot and ankle against inversion, eversion or anterior subluxation while permitting plantarflexion and dorsiflexion, and the increased pressure is released within a brief period of time after the activity stops to minimize pressure on the foot and ankle while resting.

* * * * *